United States Patent
Lavedan et al.

(10) Patent No.: US 8,865,210 B2
(45) Date of Patent: Oct. 21, 2014

(54) STABLE DOSAGE FORMULATIONS OF IMIDAZOLYLALKYL-PYRIDINES

(75) Inventors: Christian N. Lavedan, Potomac, MD (US); Deepak Phadke, Olathe, KS (US)

(73) Assignee: Vanda Pharmaceuticals, Inc., Washington, DC (US)

( * ) Notice: Subject to any disclaimer, the term of this patent is extended or adjusted under 35 U.S.C. 154(b) by 1160 days.

(21) Appl. No.: 12/278,298

(22) PCT Filed: Feb. 13, 2007

(86) PCT No.: PCT/US2007/062034
§ 371 (c)(1),
(2), (4) Date: Aug. 5, 2008

(87) PCT Pub. No.: WO2007/095523
PCT Pub. Date: Aug. 23, 2007

(65) Prior Publication Data
US 2009/0011011 A1   Jan. 8, 2009

Related U.S. Application Data

(60) Provisional application No. 60/772,727, filed on Feb. 13, 2006.

(51) Int. Cl.
- *A61K 31/44* (2006.01)
- *A61K 9/48* (2006.01)
- *A61K 31/70* (2006.01)

(52) U.S. Cl.
CPC ............... *A61K 31/70* (2013.01); *A61K 9/4858* (2013.01); *A61K 9/4866* (2013.01)
USPC ............................. 424/457; 424/464; 514/341

(58) Field of Classification Search
None
See application file for complete search history.

(56) References Cited

U.S. PATENT DOCUMENTS

| 4,083,978 | A | 4/1978 | Budai et al. | |
| 5,635,521 | A | 6/1997 | Giger | |
| 5,856,343 | A | 1/1999 | Giger | |
| 5,968,554 | A * | 10/1999 | Beiman et al. | 424/480 |
| 6,500,454 | B1 * | 12/2002 | Percel et al. | 424/451 |
| 6,627,223 | B2 * | 9/2003 | Percel et al. | 424/471 |
| 2003/0134848 | A1 | 7/2003 | Imoto et al. | |
| 2005/0244496 | A1 | 11/2005 | Campbell et al. | |

FOREIGN PATENT DOCUMENTS

| JP | 2005194491 A | 7/2005 |
| WO | 0181326 A1 | 11/2001 |
| WO | 0228365 A2 | 4/2002 |
| WO | 2007016203 A1 | 2/2007 |

OTHER PUBLICATIONS

JP, 08-020537 A, 1996 (see machine translation).*
European Patent Office, Supplementary European Search Report for Application No. EP07756903 dated Sep. 10, 2009, 3 pages.
Intellectual Property Office of Singapore, Search Report and Written Opinion for Application No. 200805889-3 dated Mar. 2010, 11 pages.
Patent Cooperation Treaty, PCT Notification of Transmittal of the International Search Report and the Written Opinion of the International Searching Authority, or the Declaration for Application No. PCT/US2007/62034 dated Sep. 19, 2008, 10 pages.
Patent Cooperation Treaty, PCT Notification Concerning Transmittal of International Preliminary Report on Patentability for Application No. PCT/US2007/62034 dated Oct. 30, 2008, 6 pages.

* cited by examiner

*Primary Examiner* — Patricia A Duffy
(74) *Attorney, Agent, or Firm* — Stephen F. Swinton, Jr.; Hoffman Warnick LLC

(57) ABSTRACT

Stable formulations of imidazolylalkyl-pyridines, including controlled-release formulations.

12 Claims, No Drawings

STABLE DOSAGE FORMULATIONS OF IMIDAZOLYLALKYL-PYRIDINES

CROSS-REFERENCE TO RELATED APPLICATIONS

This application claims the benefit of U.S. Provisional Patent Application No. 60/772,727, filed 13 Feb. 2006, which is hereby incorporated herein.

BACKGROUND OF THE INVENTION (1) Technical Field

The present invention relates to pharmaceutical technologies and specifically to production of solid dosage formulations of [2-(2-methylimidazole-1-yl)methyl]pyridine fumarate that exhibit satisfactory stability at ambient room temperature.

(2) Description of Related Art

[2-(2-methylimidazole-1-yl)methyl]pyridine is known, e.g., from U.S. Pat. Nos. 5,856,343 and 5,635,521, which are incorporated herein by reference.

SUMMARY OF THE INVENTION

The present invention relates to formulations of imidazolylalkyl-pyridines that are stable at room temperature and more particularly to such formulations containing [2-(2-methylimidazol-1-yl)methyl]pyridine fumarate. The invention further provides methods for the production of such formulations.

In one embodiment, a method according to the invention includes blending a quantity of [2-(2-methylimidazole-1-yl)methyl]pyridine fumarate and a quantity of at least one of the following: low-moisture grade microcrystalline cellulose, anhydrous lactose, and pre-gelatinized starch; and filling a capsule with the blended compound, wherein the resulting dosage formulation is substantially stable at room temperature.

The foregoing and other features of the invention will be apparent from the following more particular description of embodiments of the invention.

DETAILED DESCRIPTION OF THE INVENTION

The fumarate salt of [2-(2-methylimidazole-1-yl)methyl]pyridine free base is a member of the class of imidazolyl pyridines of Formula 1:

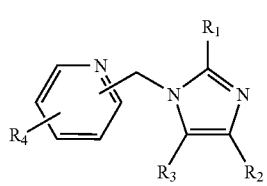

Formula 1 and pharmaceutically acceptable salts thereof,
wherein $R_1$ is hydrogen, lower alkyl, halogen with an atomic number of 9 to 35 or amino optionally mono- or disubstituted by lower alkyl, $R_2$ and $R_3$ independently of one another are hydrogen or lower alkyl, $R_4$ is hydrogen, hydroxy, lower alkyl, lower alkoxy or halogen with an atomic number of 9 to 35, in free base or acid addition salt form, and the bridge between the pyridine and the imidazole, illustrated as methylene, is methylene or ethylene.

As used herein, "lower," in the context of alkyl and alkoxy groups, denotes a radical having up to 7 carbon atoms, preferably up to 4 carbon atoms and more preferably up to 2 carbon atoms. Consequently, lower alkyl has especially up to 7 carbon atoms, preferably up to 4 carbon atoms, and in particular up to 2 carbon atoms and is, for example, methyl, ethyl, propyl, isopropyl, butyl, tert-butyl, pentyl, or hexyl. Accordingly, lower alkoxy has up to 7 carbon atoms, preferably up to 4 carbon atoms, and in particular up to 2 carbon atoms and is, for example, methoxy, ethoxy, propoxy, butoxy, tert-butoxy, pentoxy, or hexyloxy.

Insofar as above-defined, lower alkyl or lower alkoxy groups present in the compounds of Formula 1, preferably have one or two carbon atoms and especially signify methyl or methoxy. The imidazolylmethyl radical is preferably in position 2 of the pyridine. $R_1$ is preferably methyl or ethyl, more preferably methyl. $R_2$ and $R_3$ are preferably each hydrogen. $R_4$ is preferably methyl, ethyl or hydrogen, more preferably methyl or hydrogen, and in particular hydrogen.

In a particular group of compounds of formula 1, $R_1$ is lower alkyl, $R_2$ and $R_3$ independently of one another are hydrogen or lower alkyl, and $R_4$ is hydrogen, lower alkyl or halogen with an atomic number of 9 to 35.

In a further particular group of compounds of formula 1, $R_1$ is methyl, $R_2$ and $R_3$ independently of one another are hydrogen or methyl, and $R_4$ is hydrogen, methyl, or halogen with an atomic number of 9 to 35. Halogen with an atomic number of 9 to 35 denotes in particular a fluorine and chlorine residue, preferably a chlorine residue.

The compounds of Formula 1 may be present in free base form or in the form of their acid addition salts, including, for example, hydrogen fumarate and fumarate salt forms. Acid addition salts may be produced from the free bases in known manner, and vice versa.

The compounds of Formula 1 are known, e.g., from U.S. Pat. Nos. 5,856,343 and 5,635,521, which are incorporated herein by reference, or may be produced in accordance with known processes, i.e., analogously to known processes. The compound [2-(2-methylimidazole-1-yl)methyl]pyridine, exemplified in Example 1 of U.S. Pat. No. 5,635,521, is preferred. This patent describes the synthesis of [2-(2-methylimidazole-1-yl)methyl]pyridine as follows:

"9.7 g (75 mM) of 2-(chloromethyl)pyridine and 42 g (512 mM) of 2-methylimidazole are suspended in 40 ml dimethylformamide, then stirred for 3 hours at 105° C. The dimethylformamide is distilled off and the crystalline residue is diluted with ethyl acetate and a little hexane. Following filtration, the mother solution is concentrated by evaporation and the dimethylformamide distilled off, and then shaken out several times between water and methylene chloride. 10.3 g of the oily title compound are obtained."

Preparation of the fumarate salt is described as follows:

"9.3 g of the obtained base in ethanol are mixed with 12.7 g of fumaric acid. The resulting bis(base)-tris(hydrogen fumarate) crystallizes from ethanol/ethyl acetate and is recrystallized once from ethanol/ethyl acetate. It is uniform upon thin-layer chromatography and melts at 1090-1100. The fumarate is obtained analogously and melts at 120°-121°."

The inventors have discovered that the fumarate salt of the compound of Formula 1 is reasonably stable at ambient room temperature in the absence of moisture. However, when in contact with moisture, it undergoes a chemical reaction whereby a degradation product, herein referred to as DP-1, shown below, is formed.

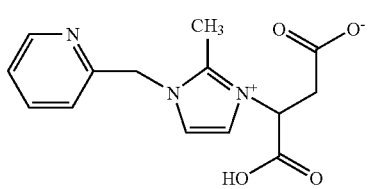

When the fumarate salt of other compounds of Formula 1 reacts in the presence of moisture, the degradation product, DP-1, will form because the chemical reaction is independent of the variable substituents, but the structure of the degradation product will differ, owing to the differences in the variable substituents.

Aqueous film-coated tablets of the fumarate salt of [2-(2-methylimidazol-1-yl)methyl]pyridine plus excipients were prepared using ethanol wet granulation for use in clinical studies. Stability data for these tablets showed satisfactory stability under refrigerated conditions, but degradation to compound DP-1 occurred at ambient temperature.

During development of the tablet formulation described above, an excipient compatibility study showed, inter a/ia, that the fumarate salt of the compound of Formula 1 was stable under dry conditions in the presence of anhydrous lactose, low-moisture grade microcrystalline cellulose, pregelatinized starch, and magnesium stearate. Accordingly, a solid formulation of the fumarate salt stable at room temperature may be produced by combining one or more of these excipients with the fumarate salt. Where low-moisture grade microcrystalline cellulose or anhydrous lactose are used, each preferably has a moisture content of less than about 1%, more preferably less than about 0.5%.

By "stable" is meant that less DP-1 is formed under similar conditions of time and temperature than when the product is prepared in the presence of water. By employing this invention, the degradation product can be reduced to amounts that are within FDA/ICH Guidance (Q3B(R) Impurities in New Drug Products, FDA/ICH guidance issued November 2003). The amount of DP-1, at 40° C./75% RH after 6 months, is less than about 1%, preferably less than about 0.5%, more preferably less than about 0.2%, and most preferably less than about 0.15%. Pharmaceutical dosages of compounds of Formula 1 may therefore be prepared that are stable at room temperature for 24 months or more.

Thus, a more stable pharmaceutical dosage unit comprising the fumarate salt or other compounds of Formula 1 as the active pharmaceutical ingredient can be prepared by eliminating or reducing the amount of moisture present during processing. For example, a more stable capsule formulation of the fumarate salt may be produced by blending together a quantity of the fumarate salt and one or more of anhydrous lactose, low-moisture grade microcrystalline cellulose, pregelatinized starch, and magnesium stearate and filling a capsule with the blended formulation. Typically, a wet granulation step or other process employing water is not necessary when manufacturing a capsule formulation of an active ingredient. However, if a granulation step is needed or desired, known methods, such as slugging or compaction, followed by grinding, may be used instead of wet granulation.

More stable tablet formulations of the fumarate salt of the compound of Formula 1 may similarly be produced by blending together a quantity of the fumarate salt and one or more of anhydrous lactose, microcrystalline cellulose, pre-gelatinized starch, and magnesium stearate, followed by direct compression, slugging, or compaction followed by grinding.

While it is preferred to use anhydrous excipients, some degree of increased stability can be obtained merely by the avoidance or minimizing of water during processing, e.g., by avoiding wet granulation or other aqueous process steps, i.e., using dry formulation processes. The term, "dry," means substantially dry. It is not necessary that water be totally absent, or that all process steps and products be completely dry, but that the amount of water should be reduced, e.g., in comparison to a wet granulation step. Preferably, water is not introduced into the process beyond those amounts of moisture that would normally be present under ambient conditions (e.g., 60% humidity at 25° C.) and even more preferably the process is carried out under dry conditions, e.g., by using anhydrous excipients and, optionally, by reducing the relative humidity of the process environment.

The use of direct compression, slugging, compaction followed by grinding, or similar dry granulating and tablet-forming methods provides the advantage of eliminating potential contact of the blended formulation with water that may be present in a granulating liquid such as ethanol. As will be recognized by one skilled in the art, the stability of capsules or tablets produced according to the invention may be furthered by packaging the capsules or tablets with a desiccant capable of substantially removing any residual moisture present in the excipients or packaging.

The solid formulations of the invention may contain other excipients such as binding agents, fillers, tableting lubricants, disintegrants, preserving agents, sweetening agents, flavoring agents, and the like, provided that such excipients do not adversely affect the stability of the formulation at room temperature.

The solid formulations of the invention are particularly useful as oral dosage formulations. As such, solid formulations of the invention may be formulated so as to provide quick, sustained, delayed, or otherwise controlled release of the active ingredient after administration to the patient.

Typically, a controlled release form produces delayed release at a constant release rate but other controlled release forms can produce non-constant release rates, e.g., to produce pulses of drug release over a longer period of time. For example, Sanders et al. describe the controlled release of an active agent from microspheres. See *Controlled Release of a Luteinizing Hormone-Releasing Hormone Analogue from Poly(d,l,-lactide-co-glycolide) Microspheres,* 73 J. of Pharm. Sci. (September 1984), which is incorporated herein by reference. An objective of using a controlled release product is to obtain a satisfactory drug response while simultaneously reducing the frequency of the drug's administration and/or the peak plasma concentrations.

Compositions for the controlled release of drugs are well known in the art. Generally, such compositions contain medicament particles mixed with or covered by a coating material that is temporarily resistant to degradation or disintegration in the stomach and/or in the intestine. Release of the medicament may occur by leaching, erosion, rupture, diffusion, or similar actions, depending upon, inter alia, the nature and thickness of the coating material. In some dosages, a medicament is coated onto spherical particles, such as dicalcium phosphate (DCP), which are in turn enclosed within gelatin capsules or compressed into tablets. One or more coatings may optionally be applied to the medicament-coated particles. Generally, such coatings are used to improve the stability of the dosage and/or enable enteric release of the medicament.

Pulsatile drug delivery formulations are dosage forms that are designed to release drug intermittently at more or less predetermined time intervals. See, for example, Bussemer et al., Crit. Rev. Ther. Drug Carrier Syst. 18(5):433-458 (2001); Gothoskar et al., "Pulsatile Drug Delivery Systems, A Review," Drug Delivery Technology 4(5): 64-69 (2004); Percel et al., US 20050118268, Parikh et al., US 20050095294, and Sharma, US 20050244497, each of which is incorporated herein by reference as though fully set forth.

The particular dosage form of a medicament can significantly affect its bioavailability, i.e., the amount of medicament released from the dosage and available for use by the body. Such differences in bioavailability can lead to significant differences in the efficacy of treatment. For example, where the medicament has a low solubility in biological fluids, its rate of absorption, and therefore its efficacy, is largely dependent upon the dosage dissolution rate. Similarly, where the high bioavailability of a medicament is capable of producing undesirable effects, a dosage form with a lower dissolution rate may be used. Accordingly, it is possible to alter the efficacy and/or side effects of a medicament by altering its dosage form.

The controlled release dosages of the present invention may employ any number of controlled release technologies for oral delivery. For example, Lalla and Bhat describe a method of, inter alia, coating DCP granules with the vasodilator isosorbide dinitrate to slow its release. Using such a method in preparing the dosage forms of the present invention comprises first spraying DCP granules with a sugar syrup and sorting the coated granules to select those having diameters between about 500 and about 600 μm. Next, a coating of a compound of Formula 1 is sprayed onto the surfaces of the granules and the granules allowed to dry. Finally, the dried Formula 1-coated granules are enclosed within a capsule, preferably a gelatin capsule. Alternatively, the dried granules may be pressed into a tablet. See, J. K. Lalla & Shruti U. Bhat, *Controlled-Release Isosorbide Dinitrate Pellets. Part I: Design and Evaluation of Controlled-Release Capsule Dosage Form*, J. PHARM. SCI., 82(12):1288-1291 (1993); J. K. Lalla & Shruti U. Bhat, *Controlled-Release Isosorbide Dinitrate Pellets. Part II: In Vivo Studies*, J. PHARM. SCI., 82(12):1292-1295 (1993), both of which are hereby incorporated by reference.

U.S. Pat. No. 5,968,554 to Beiman, et al. teaches a multi-layered controlled release dosage capable of delivering a pharmaceutical to both the stomach and the duodenum. Similarly, U.S. Pat. No. 6,312,728, also to Beiman, et al., teaches a multi-layered controlled release dosage capable of delivering a pharmaceutical to both the duodenum and large intestine or colon or to the stomach, duodenum, and large intestine or colon. Both references are incorporated herein by reference.

A number of related controlled-release dosages and methods have been described by Percel et al. For example, U.S. Pat. No. 6,627,223 describes a pharmaceutical dosage comprised of timed, sustained-release (TSR) beads having at least two coated membrane barriers, the composition and thickness of the barriers determining the lag time and duration of drug release. In one embodiment, a first membrane barrier is an enteric polymer and a second membrane is a mixture of a water-insoluble polymer and an enteric polymer. Such a configuration permits one or more pulses of a therapeutic agent in a plasma concentration-time profile.

U.S. Pat. No. 6,500,454, also to Percel et al., describes a dosage unit for providing a circadian-like release of propranolol to mimic the time-dependent physiological need for the drug. U.S. Pat. No. 6,663,888, also to Percel et al., describes a similar dosage for the circadian-like release of a histamine H2 antagonist. Each of the Percel et al. references above is incorporated herein by reference.

U.S. Pat. No. 6,569,311 to Dobetti describes a fast-disintegrating tablet comprising a drug in a multi-particulate form and having improved structural integrity/friability. This reference is also incorporated herein by reference.

Other controlled-release methods known in the art are within the scope of the present invention, including, for example, conventional pan coating, perforated pan coating, fluidized-bed coating, top-spray coating, bottom-spray coating, and tangential-spray coating. See, e.g., Atul M. Mehta & David M. Jones, *Coated Pellets Under the Microscope*, PHARM. TECH., June 1985, which is also hereby incorporated by reference. Various excipients may be incorporated into the controlled-release dosage form of the invention. Such excipients include, for example, Eudragit®, ethylcellulose, Ethocel®, triethyl citrate, hydroxypropyl methylcellulose (HPMC), polyvinylpyrrolidone (PVP), and sugars. Generally, such excipients would comprise the bulk of a controlled-release dosage.

Compositions according to the present invention are preferably formulated in a unit dosage form, each dosage containing from about 0.1 to 800 mg of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier. Each unit dose form may not alone comprise an effective amount; for example, it may be necessary to administer two tablets or capsules at the same time or at different times of the day to achieve an effective dose in the bloodstream of a patient.

Also, preferably, the pharmaceutical dosage units of the invention are packaged and stored under conditions of low humidity. To facilitate achievement of this object, the dosage units of the invention can be packaged with a desiccant.

The dosage units of the invention can comprise one or more active pharmaceutical ingredients additional to the fumarate salt of the compound of Formula 1.

Before a fumarate salt of a compound of Formula 1 can be sold as a drug, it will be necessary to conduct non-clinical and clinical studies and apply for and obtain regulatory approval from, e.g., the U.S. Food and Drug Administration for sale in the United States, or similar agencies in other jurisdictions for sale in those jurisdictions. Among the information that must be submitted to such regulatory agencies in the application process is information on how the drug product is manufactured. Thus, it is an aspect of this invention to include in such manufacturing information a process description in which water is not used in the process or, more preferably, in which the formulation of the drug is carried out under dry conditions, e.g., employing the use of anhydrous excipients in the manufacturing and formulation process and/or controlling the relative humidity during the manufacturing and formulation process. It is also an aspect of this invention to set a specification for the maximum amount of DP-1 in the drug product, i.e., in the formulated drug in unit dosage form. The specification should be set at a maximum limit not to exceed the maximum limit set by or acceptable to the regulatory agency in the jurisdiction in which approval is sought, e.g., such as are described in FDA/ICH Guidance (Q3B(R) Impurities in New Drug Products, FDA/ICH guidance issued November 2003).

Thus, a method of manufacturing in accordance with this invention comprises controlling process conditions such that the amount of DP-1 does not exceed such limits. It is also an aspect of this invention to use DP-1 as a standard for detecting and measuring the amount of DP-1 in a given production batch. It is also an aspect of this invention to seek regulatory approval for a fumarate salt of a compound of Formula 1 comprising setting a specification for DP-1 as discussed above. Such specification can pertain to the bulk drug substance, i.e., prior to formulating with excipients, or it can pertain to the drug product, i.e., the fumarate salt mixed with excipients. It is also an aspect of this invention to submit a monograph for a fumarate salt of a compound of Formula 1, e.g., a monograph for submission to the U.S. Pharmacopeia or the European Pharmacopeia, which mongraph specifies a maximum amount of DP-1.

Illustrative examples of stable formulations according to the invention are shown below in Tables 1-6. The components in each example may be dry blended and then transferred to hard gelatin capsules.

TABLE 1

Stable Formulation 1

| Ingredient | % w/w | mg/capsule | Qty. (g) |
|---|---|---|---|
| Fumarate salt of Formula 1 | 12.0 | 20.0 | 180 |
| Lactose Anhydrous | 83.5 | 139 | 1252.5 |
| Sodium Starch Glycolate | 4.00 | 6.68 | 60.0 |
| Magnesium Stearate | 0.50 | 0.84 | 7.5 |
| Hard Gelatin Capsule Size 3 | X | X | X |
| Total | 100 | 167 | 1500 |

TABLE 2

Stable Formulation 2

| Ingredient | % w/w | mg/capsule | Qty. (g) |
|---|---|---|---|
| Fumarate salt of Formula 1 | 12.0 | 20.0 | 180 |
| Avicel PH112 (microcrystalline cellulose) | 83.5 | 139 | 1252.5 |
| Sodium Starch Glycolate | 4.00 | 6.68 | 60.0 |
| Magnesium Stearate | 0.50 | 0.84 | 7.50 |
| Hard Gelatin Capsule Size 3 | X | X | X |
| Total | 100 | 167 | 1500 |

TABLE 3

Stable Formulation 3

| Ingredient | % w/w | mg/capsule | Qty. (g) |
|---|---|---|---|
| Fumarate salt of Formula 1 | 12.0 | 20.0 | 180 |
| Lactose Anhydrous | 53.5 | 139.0 | 802.5 |
| Avicel PH112 (microcrystalline cellulose) | 30.0 | 50.1 | 450 |
| Sodium Starch Glycolate | 4.00 | 6.68 | 60.0 |
| Magnesium Stearate | 0.50 | 0.84 | 7.5 |
| Hard Gelatin Capsule Size 3 | X | X | X |
| Total | 100 | 167 | 1500 |

TABLE 4

Stable Formulation 4

| Ingredient | % w/w | mg/capsule | Qty. (g) |
|---|---|---|---|
| Fumarate salt of Formula 1 | 25.0 | 41.75 | 375 |
| Lactose Anhydrous, NF | 70.5 | 117.7 | 1058 |
| Sodium Starch Glycolate | 4.00 | 6.68 | 60.0 |
| Magnesium Stearate 5712 | 0.50 | 0.835 | 7.50 |
| Hard Gelatin Capsule Size 3 | X | X | X |
| Total | 100 | 167 | 1500 |

TABLE 5

Stable Formulation 5

| Ingredient | % w/w | mg/capsule | Qty. (g) |
|---|---|---|---|
| Fumarate salt of Formula 1 | 25.0 | 41.75 | 375 |
| Avicel PH112 (microcrystalline cellulose) | 70.5 | 117.7 | 1058 |
| Sodium Starch Glycolate | 4.00 | 6.68 | 60.0 |
| Magnesium Stearate 5712 | 0.50 | 0.835 | 7.50 |
| Hard Gelatin Capsule Size 3 | X | X | X |
| Total | 100 | 167 | 1500 |

TABLE 6

Stable Formulation 6

| Ingredient | % w/w | mg/capsule | Qty. (g) |
|---|---|---|---|
| Fumarate salt of Formula 1 | 25.0 | 41.75 | 375 |
| Lactose Anhydrous, NF | 45.5 | 76.0 | 682.5 |
| Avicel PH112 (microcrystalline cellulose) | 25.0 | 41.75 | 375 |
| Sodium Starch Glycolate | 4.00 | 6.68 | 60.0 |
| Magnesium Stearate 5712 | 0.50 | 0.835 | 7.50 |
| Hard Gelatin Capsule Size 3 | X | X | X |
| Total | 100 | 167 | 1500 |

Stable formulations 4-6, shown above in Tables 4-6 were found to be stable over six months under both normal and accelerated conditions. Such stability, as well as the stabilities of other formulations, may be further improved by the use of a desiccant (e.g., silica gel canisters) in the packages in which the dosages are stored.

While this invention has been described in conjunction with the specific embodiments outlined above, it is evident that many alternatives, modifications and variations will be apparent to those skilled in the art. Accordingly, the embodiments of the invention as set forth above are intended to be illustrative, not limiting. Various changes may be made without departing from the spirit and scope of the invention as defined in the following claims.

What is claimed is:

1. A method of preparing a solid dosage formulation containing a quantity of [2-(2-methylimidazol-1-yl)methyl]pyridine fumarate comprising:
   admixing a quantity of [2-(2-methylimidazol-1-yl)methyl]pyridine fumarate with at least one excipient without contacting said [2-(2-methylimidazol-1-yl)methyl]pyridine fumarate with water; and
   forming the admixed fumarate salt and the at least one excipient into a solid dosage formulation,
   wherein the solid dosage formulation includes less than about 1% of a degradation product of Formula II when stored at 40° C. and 75% relative humidity for six months

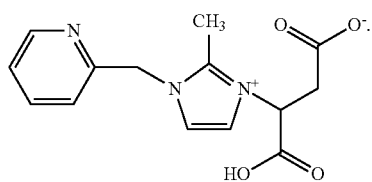

Formula II

2. The method of claim 1, wherein admixing is carried out under dry conditions.

3. The method of claim 2, wherein the at least one excipient is anhydrous.

4. The method of claim 1, wherein the at least one excipient is selected from a group consisting of: low-moisture grade microcrystalline cellulose, anhydrous lactose, pre-gelatinized starch, and magnesium stearate.

5. The method of claim 1, wherein forming the admixed fumarate salt and the at least one excipient into a solid dosage formulation includes filling a capsule with the admixture.

6. The method of claim 1, wherein forming the admixed fumarate salt and the at least one excipient into a solid dosage formulation includes forming the admixture into a tablet.

7. The method of claim 1, further comprising:
adding to the admixed material a quantity of magnesium stearate.

8. The method of claim 1, further comprising:
granulating the admixed material.

9. The method of claim 8, wherein granulating includes at least one step selected from a group consisting of: direct compression, slugging, and compaction followed by grinding.

10. The method of claim 1, further comprising:
incorporating the admixed material into a controlled-release formulation.

11. The method of claim 10, wherein the controlled-release formulation is selected from a group consisting of: a fast-disintegrating formulation, a delayed-release formulation, a sustained-release formulation, a pulsatile-release formulation, and a circadian-like release formulation.

12. The method of claim 10, wherein the at least one excipient is selected from a group consisting of: low-moisture grade microcrystalline cellulose, anhydrous lactose, pre-gelatinized starch, anionic and cationic polymers of methacrylic acid, copolymers of acrylates and methacrylates, ethylcellulose, triethyl citrate, hydroxypropyl methylcellulose (HPMC), polyvinylpyrrolidone (PVP), and sugars.

\* \* \* \* \*